United States Patent [19]

Sircar et al.

[11] 4,261,996
[45] Apr. 14, 1981

[54] PYRAZOLO[5,1-B]QUINAZOLIN-9-(4H)-ONES AND ANTI-ALLERGIC PHARMACEUTICAL COMPOSITIONS CONTAINING THEM

[75] Inventors: Jagadish C. Sircar, Ann Arbor; Thomas Capiris, Plymouth, both of Mich.

[73] Assignee: Warner-Lambert Company, Morris Plains, N.J.

[21] Appl. No.: 111,148

[22] Filed: Jan. 11, 1980

Related U.S. Application Data

[63] Continuation-in-part of Ser. No. 19,020, Mar. 8, 1979, abandoned, which is a continuation of Ser. No. 6,044, Jan. 24, 1979, abandoned.

[51] Int. Cl.³ .................. A61K 31/505; C07D 487/04
[52] U.S. Cl. .................................... 424/251; 544/250; 562/432
[58] Field of Search .................... 544/250; 424/251

[56] References Cited

U.S. PATENT DOCUMENTS

| 3,150,136 | 9/1964 | Wolfram et al. | 544/250 |
| 3,157,655 | 11/1964 | Takamizawa et al. | 544/281 |
| 3,167,537 | 1/1965 | Menzel et al. | 544/250 X |
| 3,887,559 | 6/1975 | Hardtmann | 544/250 |
| 4,017,625 | 4/1977 | Kadin | 424/251 |
| 4,033,961 | 7/1977 | Schwender et al. | 544/252 |
| 4,112,098 | 9/1978 | Vogt | 424/251 |

OTHER PUBLICATIONS

Menzel et al., Chemical Abstracts, vol. 56, 4904g (1962).

Primary Examiner—Donald G. Daus
Assistant Examiner—Diana G. Rivers
Attorney, Agent, or Firm—Stephen I. Miller

[57] ABSTRACT

Certain pyrazolo[5,1-b]quinazolin-9-(4H)-ones are disclosed. These compounds prevent the allergic response in mammals. Novel alkylthioanthranilic acids, useful as intermediates, are also disclosed.

17 Claims, No Drawings

PYRAZOLO[5,1-B]QUINAZOLIN-9-(4H)-ONES AND ANTI-ALLERGIC PHARMACEUTICAL COMPOSITIONS CONTAINING THEM

CROSS REFERENCE TO RELATED APPLICATION

This application is a continuation-in-part of our pending application Ser. No. 019,020, filed Mar. 8, 1979, now abandoned which in turn is a continuation of our application Ser. No. 006,044, filed Jan. 24, 1979, which is now abandoned.

BACKGROUND OF THE INVENTION

United States Patents Nos. 3,150,136 and 3,167,537 discloses, inter alia certain pyrazoloquinazolone carboxylic acids which are useful as intermediates for the preparation of dyestuffs. German Pat. No. 1,111,505 discloses substituted 2-carboxy-pyrazolo[5,1-b]quinazolin-9(4H)-ones which are useful as photographic color developers. The references do not disclose any pharmaceutical utility for these acids, nor do they disclose the tetrazoles of the present invention.

SUMMARY OF THE INVENTION

The present invention relates to a compound of the formula I:

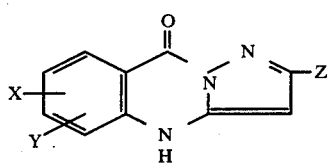

wherein X is hydrogen, hydroxy, alkyl of from 1 to 6 carbon atoms, alkoxy of from 1 to 6 carbon atoms, halo, trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; Z is COOH or

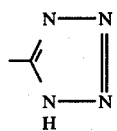

and the pharmaceutically acceptable salts thereof; provided that when X and Y are hydrogen Z may not be COOH.

The invention also relates to a pharmaceutical composition comprising an anti-allergic effective amount of a compound of the formula I:

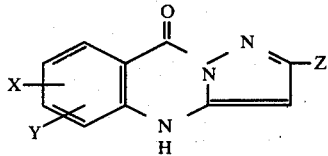

wherein X is hydrogen, hydroxy, alkyl of from 1 to 6 carbon atoms, alkoxy of from 1 to 6 carbon atoms, halo, trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; Z is COOH or

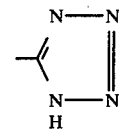

and the pharmaceutically acceptable salts thereof.

The invention also relates to a compound of the formula II:

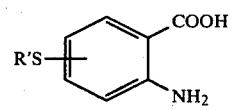

wherein R' is alkyl of from 1 to 6 carbon atoms.

The invention also relates to a method of preventing the allergic response in a mammal which comprises administering to said mammal an anti-allergic effective amount of a compound of formula I and the pharmaceutically acceptable salts thereof.

DESCRIPTION OF THE INVENTION

The tetrazoles of the invention, i.e., compounds of the formula I wherein Z is

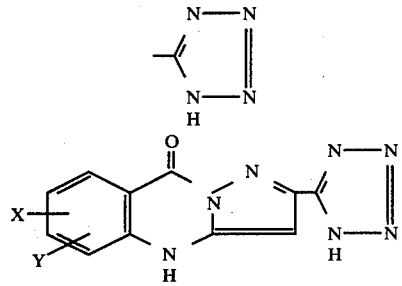

and X and Y are as defined above may be prepared from the corresponding acids or esters by methods familiar to those skilled in the art. For example, the properly substituted carboxylic acid may be converted to the corresponding acid halide such as the chloride by treatment with thionyl chloride or oxalyl chloride and converted to the acid amide by treatment with ammonia. The amide is dehydrated by treatment with, for example, phosphorous oxychloride or p-toluenesulfonyl chloride and pyridine in dimethylformamide thereby producing the corresponding nitrile which when treated with sodium azide and ammonium chloride, for example, will yield the corresponding tetrazole. The above-described amides may also be prepared directly from the corresponding esters by treatment with, for example, gaseous ammonia by methods familiar to those skilled in the art.

Other methods and reagents for converting carboxylic acids or esters into the corresponding tetrazoles will be familiar to those skilled in the art.

The above-described 2-carboxypyrazolo[5,1-b]-quinazolin-9(4H)-ones, i.e., compounds of formula I wherein Z is COOH, may be prepared by alternate procedures, which are considered equivalent for purposes of the invention. One such procedure involves the reaction of a substituted anthranilic acid of the formula

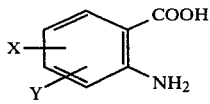

wherein X and Y are as defined above with phosgene to produce the corresponding isatoic anhydride of the formula

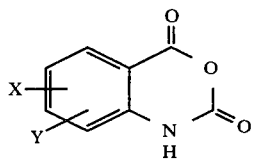

This reaction is conveniently carried out by adding, with cooling, a solution of phosgene in benzene to a solution of the anthranilic acid in, for example, dioxane/benzene (3:1). The isatoic anhydride is then converted to a 2-aminobenzoic acid hydrazide of the formula

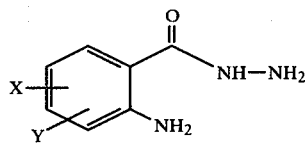

by treatment with, for example, an aqueous hydrazine hydrate solution. The hydrazide is next converted to the desired 2-carboxypyrazolo[5,1-b]quinazolin-9(4H)-ones by treatment with diethyl oxalacetate sodium salt, for example, in aqueous solution.

The alkylthio anthranilic acids of formula II which are utilized to prepare the corresponding alkylthio substituted isatoic anhydrides are novel, and may themselves be prepared by alternate procedures which are considered equivalent for purposes of the invention. One such procedure involves the steps of treating a halo-substituted 2-nitrobenzoic acid with sodium sulfide; alkylating the so produced mercaptan; followed by reduction of the nitro group thereby producing the desired alkylthio substituted anthranilic acid II. The above-described alkylated mercaptan may also be produced by treating the halo-substituted 2-nitrobenzoic acid with a mercaptide such as a sodium mercaptide. The starting halo-substituted 2-nitrobenzoic acids are either commercially available or may be prepared by methods known to those skilled in the art. For example, 5-chloro-2-nitrobenzoic acid is available from Aldrich Chemical Company, Milwaukee, Wisconsin 53233. For purposes of the invention, the preferred alkylthio anthranilic acids are represented by the following formula:

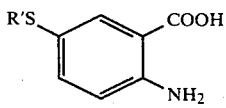

J. Pharm. Soc. Japan, 72, 76 (1952), [C.A.: 46, 11150h (1952)] discloses ethyl 5-ethylthioanthranilate.

The compounds of the invention of formula I are acids or are acidic in nature and form pharmaceutically acceptable salts with both organic and inorganic bases such as dimethylaminoethanol, the alkali metal and alkaline earth hydroxides and the alkali metal carbonates and bicarbonates such as lithium, sodium, potassium and calcium hydroxide, and the carbonates and bicarbonates of lithium, sodium and potassium. The salts are prepared by reacting an acid or a tetrazole with the desired base in the conventional manner. The tetrazoles and acids differ from their respective salts somewhat in certain physical properties such as solubility in polar solvents, but the salts are otherwise equivalent to their respective tetrazoles or acids for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The alkylthio groups, alkoxy groups and alkyl groups contemplated by the invention comprise both straight and branched carbon chains of from 1 to 6 carbon atoms. Representative of such groups are methyl, ethyl, isopropyl, pentyl, 3-methylpentyl, methoxy, ethoxy, propoxy, 1-ethylbutoxy, pentoxy, methylthio, isopropylthio, n-butylthio and the like. The term halo is intended to include fluorine, chlorine, bromine and iodine.

The compounds of the invention of formula II are new chemical substances which are of value for preparing certain of the pharmacological agents of the invention.

The compounds of the invention of formula I are new chemical substances of value as pharmacological agents which prevent the allergic response in mammals by inhibition of the release of such allergic mediators, as histamine. The assay by which this utility was established is carried out as follows.

Rat Reaginic Passive Cutaneous Anaphylaxis (PCA).

The PCA test (D. J. Herzig, P. R. Schumann, E. J. Kusner, L. Robichaud, R. E. Giles, B. Dubnick, M. von Strandtmann, S. Klutchko, M. Cohen, and J. Shavel, Jr., "Immunopharmacology", M. E. Rosenthale and H. C. Mansmann, Eds., Spectrum Publications, Inc., New York, N.Y., 1975, pp. 103–124) involved immunization of rats with 1 mg of ovalbumin intramuscularly and approximately $10^{10}$ B. pertussis organisms as pertussis vaccine, intraperitoneally. Fourteen days later, the rats were bled and the serum was prepared. Suitable dilutions of antiserum were injected intradermally at various sites on the back of rats 48 hrs before an intravenous injection of 1 mg of ovalbumin in 1 ml of physiological saline and 0.25% Evans Blue. Thirty minutes later the animals were killed in ether, the dorsal skin was reflected, and the means orthogonal diameter of the wheal was measured. For oral or intraperitoneal dosing, the drugs were suspended in 1% gum tragacanth in physiological saline and given 10–15 min before intravenous antigen challenge. For intravenous dosing, the compounds were dissolved in the saline/ovalbumin/Evans Blue solution and given with the antigen. If necessary, the compounds were first dissolved in a slight molar excess of sodium bicarbonate and then diluted into the antigen solution. Groups of five animals were used for all dose levels and control groups.

To quantitate the PCA test, the mean diameter of each wheal spot was graphed as a function of the relative anti-serum concentration. The line, fitted by the least-squares equation, was extrapolated to the value at "zero" antiserum concentration (base value). The following equation was then used to calculate the percent inhibition:

$$\left[1 - \left(\frac{\text{diameter of drug} - \text{base value}}{\text{diameter of control} - \text{base value}}\right)\right] \times 100$$

The statistical significance of the results was determined by Student's t test ($p \leq 0.05$). An inhibition of 15% was significant.

Test results obtained for several preferred compounds of the invention are as follows:
7-methoxy-2(1H-tetrazol-5-yl)-pyrazolo[5,1-b]quinazolin-9-(4H)-one shows a 100% inhibition of allergic response when administered intraperitoneally to the rat at a dose of 5 mg/kg; 4,9-dihydro-6,7-dimethoxy-9-oxopyrazolo[5,1-b]quinazoline-2-carboxylic acid shows a 100 % inhibition of the allergic response when administered intravenously to the rat at a dose of 0.1 mg/kg; 4,9-dihydro-7-fluoro-9-oxopyrazolo[5,1-b]-quinazoline-2-carboxylic acid shows a 62% inhibition of the allergic response when administered intravenously to the rat at a dose of 0.1 mg/kg; 4,9-dihydro-7-(methylsulfinyl)-9-oxo-pyrazolo[5,1-b]quinazoline-2-carboxylic acid shows a 76% inhibition of the allergic response when administered intraperitoneally to the rat at a dose of 5 mg/kg; 4,9-dihydro-7-(methylsulfony)9-oxo-pyrazolo[5,1-b]-quinazoline-2-carboxylic acid shows a 100% inhibition of the allergic response when administered intraperitoneally to the rat at a dose of 5 mg/kg.

The compositions of the invention can be administered in a variety of dosage forms such as tablets or capsules and liquids for oral or parenteral use. The dosage forms may contain, in addition to the active component, any of the usual compounding excipients such as flavors, colors, stabilizers and tableting materials such as binders, fillers, lubricants and the like. The dosage requirements may vary with the particular composition being employed and may depend on the severity of the symptoms being presented and the size of the mammal being treated. In general, an amount of from about 0.1 to about 10 mg/kg of the active component in single or divided doses will be sufficient to accomplish the method of the invention. The invention is illustrated by the following examples.

EXAMPLE 1

4,9-Dihydro-5-methoxy-9-oxo-pyrazolo[5,1-b]quinazoline-2-carboxylic acid.

A mixture of 2-amino-3-methoxybenzoic acid hydrazide (23,6 g; 0.13 mole) and 90% diethyl oxalacetate, sodium salt (32.7 g; 0.14 mole) in water (400 ml) is heated under reflux for 1.5 hrs. To the resulting yellow solution is added sodium carbonate (14.8 g; 0.14 mole) and the solution is refluxed for an additional hour. The cooled reaction mixture is cautiously treated with conc. HCl (0.28 mole) and the precipitated solid is filtered off, washed with water and recrystallized from methanol (1500 ml). Yield 5.8 g; mp 271°-272° C. (d).

EXAMPLE 2

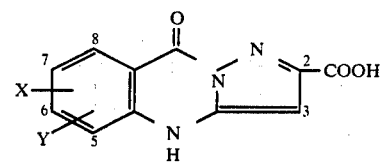

The compounds below are prepared from appropriately substituted anthranilic acid hydrazides by the procedure of Example 1.

|     | X | Y | mp | | SOLVENT FOR RECRYSTALLIZATION |
|-----|------|--------|----------------|-----|-----------|
| (a) | H | H | 315–320° C. | (d) | DMF |
| (b) | 7-Cl | H | 356–359° C. | (d) | DMF |
| (c) | 7-OCH$_3$ | H | 310–320° C. | | DMF |
| (d) | 5-CH$_3$ | H | 268–274° C. | | MeOH—H$_2$O |
| (e) | 7-CH$_3$ | H | 290–295° C. | | DMF—Et$_2$O |
| (f) | 6-OCH$_3$ | 7-OCH$_3$ | 305–308° C. | (d) | DMF |
| (g) | 7-F | H | 300° C. | | DMF |
| (h) | 8-CF$_3$ | H | 298–302° C. | | DMF—CH$_2$OH |
| (i) | 8-OCH$_3$ | H | 293–295° C. | | DMF |

EXAMPLE 3

4,9-Dihydro-7-hydroxy-9-oxo-pyrazolo[5,1-b]quinazoline-2-carboxylic acid.

A suspension of 4,9-dihydro-7-methoxy-9-oxo-pyrazolo[5,1-b]quinazoline-2-carboxylic acid (2.0 g; 0.0077 mole) in 48% hydrobromic acid (30 ml) and glacial acetic acid (50 ml) is refluxed for 23 hrs. The mixture is cooled and then diluted with water (25 ml). The product, which precipitates out, is collected by filtration and recrystallized from DMF-Ether (1:1, 90 ml). Yield 1.1 g; mp 285°–286° C. (d).

EXAMPLE 4

4,9-Dihydro-5-hydroxy-9-oxo-pyrazolo[5,1-b]quinazoline-2-carboxylic acid.

From 4,9-dihydro-5-methoxy-9-oxo-pyrazolo[5,1-b]-quinazoline-2-carboxylic acid (1.04 g), 48% hydrobromic acid (25 ml) and acetic acid (25 ml), following the procedure of Example 3, there is obtained the desired product (0.75 g) as the quarter hydrate. mp 326°–330° C.

EXAMPLE 5

4,9-Dihydro-7-methylthio-9-oxo-pyrazolo[5,1-b]quinazoline-2-carboxylic acid.

A mixture of 2-amino-5-methylthiobenzoic acid hydrazide (2.5 g; 12.7 mmole) and 90% diethyloxalacetate, sodium salt (3.27 g; 14 mmole) in water (50 ml) is heated under reflux for 2 hrs. Sodium carbonate (1.5 g; 14 mmole) solution in water (15 ml) is added to the reaction mixture and the hearing is continued for another hour. The reaction mixture is cooled, carefully acidified with conc. HCl (4 ml) and the resulting yellow precipitate is filtered, washed and dried. The product is recrystallized from methanol-water, yield 1.0 g; mp 285°–9° (d).

EXAMPLE 6

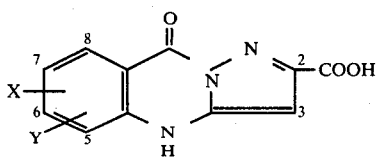

The compounds below are prepared from appropriately substituted anthranilic acid hydrazides by the procedure of Example 5.

| X | Y | mp | SOLVENT FOR CRYSTALLIZATION |
|---|---|---|---|
| 7-(CH3)2CHS | H | 275-6° (d) | DMF |
| 7-CH3(CH2)3— | H | 270-1° (d) | DMF-MeOH |
| 7-CH3O— | 5-CH3O— | 285-7° (d)[1] | DMF |
| H | 5-[S structure] | 253-5° (d)[2] | MEOH |

[1]Contains ⅛ CH3OH, 1/10 C3H7NO as solvent of crystallization.
[2]Contains 1 CH3OH as solvent of crystallization.

EXAMPLE 7

4,9-Dihydro-7-(methylsulfinyl)-9-oxo-pyrazolo[5,1-b]quinazoline-2-carboxylic acid.

A mixture of 4,9-dihydro-7-methylthio-9-oxo-pyrazolo[5,1-b]quinazoline-2-carboxylic acid (5.5 g; 0.02 mole) and 1(N) sodium hydroxide solution (25 ml) in water (500 ml) is chilled to 12° and a solution of sodium metaperiodate (4.28 g, 0.02 mole) in water (150 ml) is added. The reaction mixture is stirred at room temperature for 4 hrs and the resulting solution is cooled and treated with 1(N) HCl (30 ml). The greenish precipitate is filtered, washed and recrystallized from DMF-methanol. Yield 4.4 g; mp 285°-90° (d).

EXAMPLE 8

4,9-Dihydro-7-(butylsulfinyl)-9-oxo-pyrazolo[5,1-b]quinazoline-2-carboxylic acid, hemihydrate.

From 4,9-dihydro-7-(butylthio)-9-oxo-pyrazolo[5,1-b]quinazoline-2-carboxylic acid (3.17 g, 10 mmole), 1(N) NaOH soln (10 ml) in water (150 ml) and NaIO4 (2.14 g; 10 mmole) in water (50 ml); following the procedure of Example 7, there is obtained 4,9-dihydro-7-(butylsulfinyl)-9-oxo-pyrazolo[5,1-b]-quinazoline-2-carboxylic acid, hemihydrate (2.0 g); mp 205°-210° (d) remelts at 260° (d) after crystallization from aq. methanol.

EXAMPLE 9

4,9-Dihydro-7-(methylsulfonyl)-9-oxo-pyrazolo[5,1-b]-quinazoline-2-carboxylic acid.

A mixture of 4,9-dihydro-7-(methylthio)-9-oxo-pyrazolo[5,1-b]quinazoline-2-carboxylic acid (1.1 g; 4 mmole), in glacial acetic acid and 30% H2O2 (3 ml) is heated under reflux for 1 hr and then stirred at room temperature overnight. The tan solid is filtered off and recrystallized from DMF-ether. Yield 0.95; mp 360°-365° (d).

EXAMPLE 10

4,9-Dihydro-6,7-dihydroxy-9-oxopyrazolo[5,1-b]quinazoline-2-carboxylic acid, compound with dimethylformamide (1:1).

A mixture of 4,9-dihydro-6,7-dimethoxy-9-oxo-pyrazolo[5,1-b]quinazoline-2-carboxylic acid (1.0 g), 48% HBr (30 ml) and acetic acid (50 ml) is refluxed for 20 hours when the product crystallizes out as yellow solid. The reaction mixture is cooled, diluted with water (25 ml) and the product is filtered. The crude product is recrystallized from DMF (20 ml) and water (200 ml). Yield 350 mg; mp 282°-6° (d).

EXAMPLE 11

5-Methoxy-2-(1H-tetrazol-5-yl)-pyrazolo[5,1-b]quinazolin-9(4H)-one.

To a warm solution of 4,9-dihydro-5-methoxy-9-oxo-pyrazolo[5,1-b]quinazoline-2-carbonitrile (2.98 g; 0.0124 mole) in DMF (150 ml) is added sodium azide (2.42 g; 0.0372 mole) and ammonium chloride (1.99 g; 0.0372 mole). The reaction mixture is heated at 100° C. for 22 hrs, concentrated to ⅓ volume and then poured into ice-water mixture. The mixture is acidified to pH 1.0 with 4 (N) hydrochloric acid (15 ml) and the product filtered off. The crude product is stirred with 0.5 (N) sodium hydroxide solution (600 ml) for 1.0 h, the insoluble material filtered off and the filtrate acidified with conc. HCl (30 ml). The precipitated solid is filtered, washed with water and dried; mp 300° C. when recrystallized from DMF. Yield 0.425 g.

By the same procedure starting with the corresponding 6,7-dimethoxy compound, the product obtained is 6,7-dimethoxy-2-(1H-tetrazol-5-yl)-pyrazolo[5,1-b]-quinazolin-9(4H)-one. Similarly, starting with the 7-fluoro and 8-trifluoromethyl compounds, respectively, the products obtained are the 7-fluoro- and 8-trifluoromethyl-2-(1H-tetrazol-5-yl)-pyrazolo[5,1-b]quinazolin-9(4H)-ones.

EXAMPLE 12

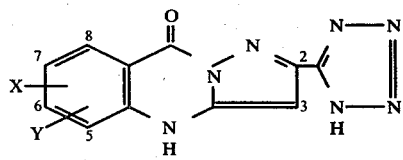

The compounds below are prepared from appropriately substituted 4,9-dihydro-9-oxo-pyrazolo[5,1-b]-quinazoline-2-carbonitriles by the procedure of Example 11.

| X | Y | mp |
|---|---|---|
| H | H | 342-345° C. (d) |
| 7-Cl | H | >300° C. |
| 7-OCH3 | H | >300° C. |

To prepare the sodium salt of the 5-methoxy compound of Example 11, the latter as the free tetrazole is dissolved with warming in an equivalent amount of 0.1 N aqueous sodium hydroxide solution, the water is evaported off and the sodium salt is dried under vacuum. The potassium, calcium and magnesium salts are prepared in the same manner.

EXAMPLE 13

5-Methylthio-2-aminobenzoic acid.

A mixture of 5-methylthio-2-nitrobenzoic acid (25.4 g; 0.119 mole), methanol (200 ml) and Raney nickel (2 g) is shaken in an atmosphere of hydrogen at 50 lb pressure when theoretical amount of hydrogen is absorbed. The catalyst is filtered off and the filtrate evaporated to dryness. The residue is recrystallized from etheriso-Pr₂O. Yield 7.6 g; mp 145°–150°.

EXAMPLE 14

5-n-butylthio-2-aminobenzoic acid.

Catalytic hydrogenation of 5-n-butylthio-2-nitrobenzoic acid (10.6 g; 0.042 mole) in methanol (120 ml) in presence of Raney nickel (1 g) by the procedure of Example 13 gives 5-n-butylthio-2-aminobenzoic acid (8.95 g), mp 69°–72°.

EXAMPLE 15

Methyl 2-amino-3-(tetrahydro-2-thienyl)benzoate.

A solution of methyl anthranilate (75.5 g; 0.5 mole) in CH₂Cl₂ (1.0 l) is cooled to −70° and a solution of tert-butyl hypochlorite (54 g; 0.5 mole) in CH₂Cl₂ (150 ml) is added slowly keeping the temperature at −70°. The resultant N-chloroanthranilate solution is stirred for 1.0 hr and then tetrahydrothiophene (110 ml) is added at such a rate as to maintain the exotherm to less than 10°. The dark solution is stirred at −70° for 2.0 hr, triethylamine (125 ml) is added dropwise, and the solution is stirred for 24 hrs. The solvents are removed and the residue is diluted with CH₂Cl₂, washed with (1 N) NaOH solution, water and dried. Removal of solvents gives an oil. Unreacted methyl anthranilate is removed under reduced pressure (b.p. 95°–100°/0.35 mm) at bath temperature at 150°. The residue is dissolved in CH₂Cl₂ and partially chromatographed through silica gel. The solid residue is recrystallized from methanol. Yield 27.0 g; mp 75°–9°.

PREPARATIVE EXAMPLES

PREPARATIVE EXAMPLE 1

3-Methoxy-2H-3,1-benzoxazine-2,4(1H)dione; (3-Methoxyisatoic Anhydride).

To a solution of 3-methoxy anthranilic acid (8.36 g; 0.05 mole) in dioxane (75 ml) and benzene (25 ml) is added a 12.5% solution of phosgene in benzene (46 g) with cooling in an ice bath. After the addition, the reaction mixture is stirred at room temperature overnight. The precipitated product is filtered off, washed with benzene and ether, dried and used without further purification. Yield 9.1 g (94%) mp 263°–264° C. (d).

PREPARATIVE EXAMPLE 2

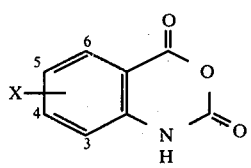

The compounds below are prepared from appropriately substituted anthranilic acids by the procedure of Preparative Example 1.

| X | mp |
|---|---|
| 3-CH₃ | 286–288° C. (d) |
| 5-CH₃ | 245–250° C. (d) |
| 5-OCH₃ | 244–247° C. (d) |
| 6-OCH₃ | 260–264° C. (d) |

PREPARATIVE EXAMPLE 3

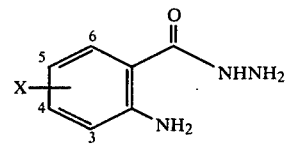

Substituted-2-aminobenzoic acid, hydrazide.

The substituted isatoic anhydride (0.14 mole) is slowly added to a cold (+5° C. to +10° C.) 18% aqueous solution of hydrazine (225 ml). During the exothermic reaction a white solid is formed. After stirring at room temperature overnight, the product is filtered off and washed with water. The hydrazide is used as is or is purified via crystallization before use.

The following compounds are prepared employing the above procedure.

| X | mp | RECRYSTALLIZATION SOLVENT |
|---|---|---|
| 3-CH₃ | 155–158° C. | — |
| 3-OCH₃ | 142–147° C. | Benzene |
| 5-CH₃ | 137–138° C. | — |
| 5-OCH₃ | 141–143° C. | Water |
| 5-Cl | 133.5–136° C. | — |
| 6-CF₃ | 120–125° C. (d) | — |
| 5-F | 248–251° C. | CH₂Cl₂—MeOH |
| 6-OCH₃ | 151–155° C. | — |

PREPARATIVE EXAMPLE 4

4,9-Dihydro-9-oxo-pyrazolo[5,1-b]quinazoline-2-carboxamide.

A mixture of 4,9-dihydro-9-oxo-pyrazolo[5,1-b]quinazoline-2-carboxylic acid (5 g; 0.022 mole), thionyl chloride (250 ml) and four drops of pyridine is stirred at room temperature for 24 hrs. The reaction mixture is evaporated to dryness under reduced pressure in a water bath at 30°–40° C. The residue is treated with cold (0° C.) concentrated ammonium hydroxide solution (200 ml) and allowed to come to room temperature. The product is filtered off, washed with ether and used in the next step without further purification. Yield 3.2 g; mp 315°–325° C. An analytical sample, recrystallized from dimethylformamide, melts at 335°–340° C. By the same procedure, starting with the corresponding 7-fluoro compound, the product obtained is 4,9-dihydro-7-fluoro-9-oxo-pyrazolo[5,1-b]quinazoline-2-carboxamide.

PREPARATIVE EXAMPLE 5

4,9-Dihydro-5-methoxy-9-oxo-pyrazolo[5,1-b]quinazoline-2-carboxamide.

A mixture of 4,9-dihydro-5-methoxy-9-oxo-pyrazolo[5,1-b]quinazoline-2-carboxylic acid (6.6 g; 0.025 mole) and phosphorous oxychloride (100 ml) is stirred at room temperature overnight. The solid is filtered off, washed with ether, dried and treated with cold (0° C.) ammonium hydroxide solution (58%; 50 ml). After standing overnight at room temperature the product is filtered off, dried and used in the next step without further purification. Yield 5.06 g; mp 265°–270° C. By the same procedure, starting with the corresponding 6,7-dimethoxy compound, the product obtained is 4,9-dihydro-6,7-dimethoxy-9-oxo-pyrazolo[5,1-b]quinazoline-2-carboxamide.

PREPARATIVE EXAMPLE 6

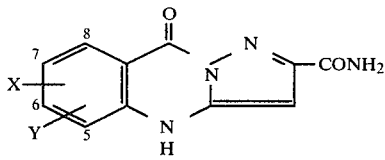

The compounds below are prepared from appropriately substituted 4,9-dihydro-9-oxopyrazolo[5,1-b]quinazoline-2-carboxylic acids by the procedures of the preceding preparative examples.

| X | Y | mp | METHOD OF PREPARATIVE EXAMPLE |
|---|---|---|---|
| 7-Cl | H | 350–360° C. | 4 |
| 7-OCH$_3$ | H | 340–355° C. | 5 |

PREPARATIVE EXAMPLE 7

4,9-Dihydro-5-methyl-9-oxo-pyrazolo[5,1-b]quinazoline-2-carboxamide.

To a solution of 4,9-dihydro-5-methyl-9-oxo-pyrazolo[5,1-b]quinazoline-2-carboxylic acid (4.86 g; 0.02 mole) in dimethylformamide (50 ml) is added 1,1'-carbonyldiimidazole (4.86 g; 0.03 mole). The reaction mixture is heated at 100° C. for 12 min, then cooled and diluted with ether (75 ml) and methylene chloride (25 ml). The tan solid is filtered off and suspended in cold (0° C.) DMF (50 ml). Anhydrous ammonia is bubbled through for 10 min and the resulting solution is allowed to stand at room temperature overnight. The dimethylformamide solution is evapoated to dryness under reduced pressure and the residue is washed with methylene chloride and ether and dried. Yield 3.0 g; mp 340°–345° C. (d). By the same procedure, starting with the corresponding 8-trifluoromethyl compound, the product obtained is 4,9-dihydro-8-trifluoromethyl-9-oxo-pyrazolo[5,1-b]quinazoline-2-carboxamide.

PREPARATIVE EXAMPLE 8

4,9-Dihydro-5-methoxy-9-oxo-pyrazolo[5,1-b]quinazolinecarbonitrile.

A suspension of 4,9-dihydro-5-methoxy-9-oxo-pyrazolo[5,1-b]quinazoline-2-carboxamide (5.05 g; 0.0195 mole) in phosphorous oxychloride (100 ml) is heated under reflux for 2 hrs. After standing two days at room temperature, excess phosphorous oxychloride is removed under reduced pressure and the residue suspended in saturated sodium bicarbonate solution (100 ml). The solid is filtered off, washed with water and dried. Yield 3.0 g; mp 292°–297° C. (d). Starting with the corresponding 7-fluoro, 8-trifluoromethyl and 6,7-dimethoxy compounds, the products obtained are, respectively, the 7-fluoro, 8-trifluoromethyl and 6,7-dimethoxy-4,9-dihydro-9-oxo-pyrazolo[5,1-b]quinazoline-2-carbonitriles.

PREPARATIVE EXAMPLE 9

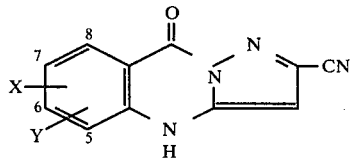

The compounds below are prepared from appropriately substituted 4,9-dihydro-9-oxo-pyrazolo[5,1-b]quinazoline-2-carboxamides by the procedure of Preparative Example 8.

| X | Y | mp | SOLVENT OF RECRYSTALLIZATION |
|---|---|---|---|
| H | H | 365–375° C. (d) | DMF |
| 7-Cl | H | 400–405° C. (d) | DMF |
| 7-OCH$_3$ | H | 343–346° C. (d) | — |
| 5-CH$_3$ | H | 335–345° C. (d) | — |

PREPARATIVE EXAMPLE 10

5-Methylthio-2-nitrobenzoic acid.

5-Chloro-2-nitrobenzoic acid (100.8 g; 0.5 mole) is dissolved in water (1.0 l) and 4(N) sodium hydroxide solution (83 ml) (pH 7.5). A solution of Na$_2$S.9H$_2$O (132 g; 0.55 mole) in water (300 ml) is added and the mixture is heated at 50°–55° for 2.5 hrs. The reaction mixture is then treated with 20% sodium hydroxide solution (100 ml) and dimethyl sulfate (126.2 g; 1.0 mole) and is heated under reflux for 10 hrs. On cooling and acidification with (4 N) HCl (160 ml), the product precipitates out as a yellow solid (101.5 g) which is recrystallized from ether; mp 175°–8°.

PREPARATIVE EXAMPLE 11

Substituted 2-nitrobenzoic acid.

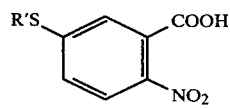

The compounds below are prepared from 5-chloro-2-nitrobenzoic acid, sodium sulfide and appropriate alkyl halides (R'X) by the procedure of Preparative Example 10.

| R' | R'X | mp |
|---|---|---|
| (CH$_3$)$_2$CH— | (CH$_3$)$_2$CHBr | 133–9° |
| CH$_3$(CH$_2$)$_3$— | n-C$_4$H$_9$Br | 105–110° |

PREPARATIVE EXAMPLE 12

Methyl 2-amino-3,5-dimethoxybenzoate.

A mixture of methyl 3,5-dimethoxy-2-nitrobenzoate (Ger 501,609, April 2, 1927; CA. 24, 47929) (39.0 g; 0.162 mole), 5% Pd on charcoal (2.0 g), methanol (200 ml) and tetrahydrofuran (200 ml) is shaken in an atmosphere of hydrogen at 52 lb pressure for 46 h when

PREPARATIVE EXAMPLE 13

6-Methylthio-2H-3,1-benzoxazine-2,4-(1H)-dione.

5-Methylthio-2-nitrobenzoic acid (53.25 g; 0.25 mole) is added to a solution of stannous chloride (225.6 g; 1.0 mole) in conc. HCl (340 ml) and the reaction mixture is brought to 110° and then cooled and concentrated. The concentrate is brought to pH 13 cautiously with 4(N) NaOH. The mixture is then filtered through supercel and the pH of the filtrate is adjusted to 6.7 and refiltered. The filtrate is cooled and is then treated with 12.5% phosgene in benzene solution. (400 ml). The precipitated solid is filtered, washed and dried. Yield 30.6 g; mp 216°–8°.

PREPARATIVE EXAMPLE 14

6-(isopropylthio)-2H-3,1-benzoxazine-2,4-(1H)-dione.

From 5-isopropylthio-2-nitrobenzoic acid (12.05 g), following the procedure of preparative example 13, there is obtained 5-isopropylthioisatoic anhydride (7.45 g), mp 219°–221° (d).

PREPARATIVE EXAMPLE 15

6-n-butylthio-2H-3,1-benzoxazine-2,4-(1H)-dione.

A solution of phosgene (12.5%) in benzene (40 g; 0.05 mole) is added to a cooled (5°) solution of 5-n-butylthio-anthranilic acid (8.9 g; 0.0395 mole) in dioxane (150 ml) and benzene (80 ml). The mixture is stirred at room temperature overnight and the pale green crystals are filtered off and dried. Yield 6.85 g; mp 196°–200°.

PREPARATIVE EXAMPLE 16

6,8-Dimethoxy-2H-3,1-benzoxazine-2,4-(1H)-dione.

A mixture of methyl 3,5-dimethoxy anthranilate (21.2 g; 0.1 mole) and 1(N) sodium hydroxide solution (100 ml) is refluxed for 2.0 hrs, cooled and is buffered with dry ice. The solution is treated with 12.5% phosgene in benzene (110 ml) in an ice bath. The mixture is stirred for 4.0 hrs, filtered off the product and dried in vacuo. Yield 22.0 g; mp 263°–5° (d).

PREPARATIVE EXAMPLE 17

8-(Tetrahydro-2-thienyl)-2H-3,1-benzoxazine-2,4-(1H)-dione.

From methyl 2-amino-3-(tetrahydro-2-thienyl)-benzoate (10 g; 0.042 mole), following the procedure of preparative example 16, there is obtained 8-(tetrahydro-2-thienyl)-2H-3,1-benzoxazine-2,4-(1H)-dione (6.0 g), mp 195°–9° (d).

PREPARATIVE EXAMPLE 18

5-Methylthio-2-aminobenzoic acid hydrazide.

6-methylthio-2H-3,1-benzoxazine-2,4-(1H)-dione (25.11 g; 0.72 mole) is added to a cold solution of 54.4% hydrazine (75 ml) in water (75 ml). After stirring at room temperature overnight, the while solid is filtered, washed with cold water and dried. Yield 21.3 g; mp 124°–127°.

PREPARATIVE EXAMPLE 19

Substituted-2-aminobenzoic acid hydrazide.

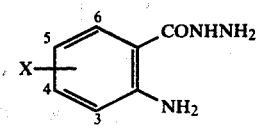

The following compounds are prepared using appropriately substituted isatoic anhydride and following the procedure of Preparative Example 18.

| X | mp |
| --- | --- |
| 5-(CH$_3$)$_2$CHS— | 110–115° |
| 5-CH$_3$(CH$_2$)$_3$S— | 92–95° |
| 3,5-(CH$_3$O)$_2$— | 137–141° |
| 3-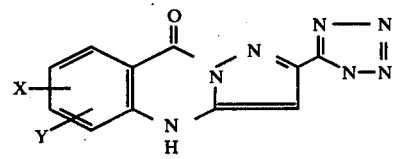 | 123–7° |

We claim:
1. A compound of the formula:

wherein X is hydrogen, hydroxy, alkyl of from 1 to 6 carbon atoms, alkoxy of from 1 to 6 carbon atoms, halo, trifluoromethyl, or SO$_n$R wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; and the pharmaceutically acceptable salts thereof.

2. The compound as defined in claim 1 which is 7-methoxy-2-(1H-tetrazol-5-yl)-pyrazolo[5,1-b]quinazolin-9(4H)-one and the pharmaceutically acceptable salts thereof.

3. The compound as defined in claim 1 which is 2-(1H-tetrazol-5-yl)-pyrazolo[5,1-b]quinazolin-9(4H)-one and the pharmaceutically acceptable salts thereof.

4. A pharmaceutical composition comprising an antiallergic effective amount of a compound of the formula I:

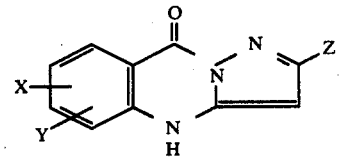

wherein X is hydrogen, hydroxy, alkyl of from 1 to 6 carbon atoms, alkoxy of from 1 to 6 carbon atoms, halo trifluoromethyl, or SO$_n$R wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; Z is COOH or

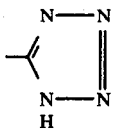

and the pharmaceutically acceptable salts thereof.

5. The pharmaceutical compositions as defined in claim 4 wherein Z is

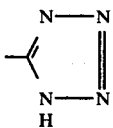

6. The pharmaceutical compositions as defined in claim 4 wherein Z is COOH.

7. The compound defined in claim 1 which is 5-methoxy-2-(1H-tetrazol-5-yl)pyrazolo[5,1-b]quinazolin-9(4H)-one, and the pharmaceutically acceptable salts thereof.

8. The compound defined in claim 1 which is 7-chloro-2-(1H-tetrazol-5-yl)pyrazolo[5,1-b]quinazolin-9(4H)-one, and the pharmaceutically acceptable salts thereof.

9. The pharmaceutical composition defined in claim 6 wherein X is 5-methoxy and Y is hydrogen.

10. The pharmaceutical composition defined in claim 6 wherein X is 7-methoxy and Y is hydrogen.

11. The pharmaceutical composition defined in claim 6 wherein X is 5-hydroxy and Y is hydrogen.

12. The pharmaceutical composition defined in claim 6 wherein X is 8-trifluoromethyl and Y is hydrogen.

13. The pharmaceutical composition defined in claim 6 wherein X is 7-methylsulfonyl and Y is hydrogen.

14. The pharmaceutical composition defined in claim 6 wherein X is 7-methylsulfinyl and Y is hydrogen.

15. The pharmaceutical composition defined in claim 6 wherein X is 6-hydroxy and Y is 7-hydroxy.

16. The pharmaceutical composition defined in claim 6 wherein X is 6-methoxy and Y is 7-methoxy.

17. The pharmaceutical composition defined in claim 6 wherein X is 7-fluoro and Y is hydrogen.

* * * * *